(12) United States Patent
Liang et al.

(10) Patent No.: US 8,461,355 B2
(45) Date of Patent: Jun. 11, 2013

(54) PREPARATION METHOD OF 3,4-ETHYLENEDIOXYTHIOPHENE

(75) Inventors: Nai-Yun Liang, Zhongli (TW); Hui-Shan Tsai, Zhongli (TW); Ching-Wei Ke, Zhongli (TW); Chin-Wan Jseng, Zhongli (TW)

(73) Assignee: Far Eastern New Century Corporation, Taipei (TW)

( * ) Notice: Subject to any disclaimer, the term of this patent is extended or adjusted under 35 U.S.C. 154(b) by 0 days.

(21) Appl. No.: 13/342,541

(22) Filed: Jan. 3, 2012

(65) Prior Publication Data

US 2013/0023673 A1    Jan. 24, 2013

(30) Foreign Application Priority Data

Jul. 19, 2011  (TW) .................................. 100125479

(51) Int. Cl.
*C07D 495/04* (2006.01)
(52) U.S. Cl.
USPC ........................................................ 549/50
(58) Field of Classification Search
USPC ........................................................ 549/50
See application file for complete search history.

(56) References Cited

PUBLICATIONS

Elschner, A., et al. "Chapter 5: The Synthesis of EDOT Monomer, and Its Physical and Chemical Properties," PEDOT: Principles and Applications of an Intrinsically Conductive Polymer. CRC Press, Published Nov. 2, 2010, pp. 47-66.*

Lidstrom, P., et al. "Microwave assisted organic synthesis-a review." Tetrahedron 57 (2001), pp. 9225-9283.*
Wiley & Sons Publishers. Name Reactions in Heterocyclic Chemistry. (c) 2005. <<Available at: http://books.google.com/books?id=1N-MZVSesTcC&pg=PA199&Ipg=PA199&dq=Hinsberg+condensation&source=bl&ots=uiS9p5fc9r&sig=IhoWzdosKGIa__mKkFI3Q4 hgQQvM&hI=en&sa=X&ei=9gHCUJnHNsqLOQGVOICYCA&ved=0CCsQ6AEwAA#v=onepage&q&f=false>>.*
Alaviuhkola, T. "Aromatic Borate Anions and Thiophene Derivatives for Sensor Applications." Dissertation thesis. ACTA Universitatis Ouluensis. Published Dec. 29, 2009.*
Organic Chemistry Portal. "Fischer Esterification." Published Feb. 11, 2010. Available at: <http://web.archive.org/web/20100211142428/http://www.organic-chemistry.org/namedreactions/fischer-esterification.shtm>.*
Fredrik von Kieseritzky, Fredrik Allared, Emma Dahlstedt and Jonal Hellberg. "Simple one-step sythesis of 3,4-dimethoxythiophene and its conversion into 3,4-ethylenedioxythiophene (EDOT)". Tetrahedron Letters 45 (2004) 6049-6050.
Joan Halfpenny, PHillip B. Rooney and Zachary S. Sloman. "Optimisation of substitution at the 2- and 5- positions of 3,4-dialkoxythiophenes via the Mannich reaction: the influences of steric crowding, electrophile reactivity and temperature". J. Chem. Soc., Perkin Trans. 1, 2001, 2595-2603.
L. "Bert" Groenendaal, Friedrich Jonas, Dieter Freitag, Harald Pielartzik, and John R. Reynolds. "Poly(3,4-ethylenedioxythiophene) and Its Derivatives: Past, Present and Future". Adv. Mater. 2000, 12, No. 7, pp. 481-494.

* cited by examiner

*Primary Examiner* — Andrew D Kosar
*Assistant Examiner* — John S Kenyon
(74) *Attorney, Agent, or Firm* — McClure, Qualey & Rodack, LLP

(57) ABSTRACT

A method of preparing 3,4-ethylenedioxythiophene is provided. The preparation is performed by microwave heating to greatly increase the yield and decrease the reaction time, energy consumption, solvent usage, and environmental damage.

10 Claims, No Drawings

PREPARATION METHOD OF 3,4-ETHYLENEDIOXYTHIOPHENE

CROSS-REFERENCE TO RELATED APPLICATION

This application claims the priority benefit of Taiwan application serial no. 100125479, filed Jul. 19, 2011, the full disclosure of which is incorporated herein by reference.

BACKGROUND

1. Technical Field

The disclosure relates to a method of preparing 3,4-ethylenedioxythiophene. More particularly, the disclosure relates to a method of preparing 3,4-ethylenedioxythiophene by microwaving instead of conventional heating.

2. Description of Related Art 3,4-ethylenedioxythiophene (EDOT) is conventionally used as a monomer to prepare Poly(3,4-ethylenedioxythiophene) (PEDOT). Since PEDOT has the properties of high conductivity, high transparency, good heat resistance, good hydrolysis resistance, and easy processing, PEDOT is widely used in photoelectric applications, such as organic light emitting diodes (OLEDs), solar cells, organic thin film transistors (OTFT), super capacitors, and electron transporting layers of flexible electronic papers etc., Many synthesis methods of EDOT have been studied and discussed by many scholars. However, the EDOT synthesis methods still have problems of low yield, long reaction time or environmental damage etc.

Early in 2000, Groenendaal and Jonas et al. had disclosed a method of heating 2,2'-thiodiacetic acid to perform the esterification, condensation, etherification, hydrolysis, and decarboxylation reactions of EDOT synthesis process. Although the supply source of the starting material was quite stable and the reaction condition wais mild, the problems of long reaction time and low yield made this method cannot efficiently produce EDOT (*Adv. Mater.* 2000, 12, 481).

In 2004, Fredrik et al. disclosed a method having easier steps to synthesize EDOT. However, the starting material, 2,3-dimethoxy-1,3-butadiene, could not be easily obtained and was high price.

Hence, the greatly increased cost did not facilitate mass production by the industry (*Tetrahedron Letters* 2004, 45, 6049).

Furthermore, many other scholars studied various starting materials, solvents, or catalysts to improve the yield of a certain step in the EDOT is synthesis and thus the EDOT yield. For example, in 2001, Halfpenny used disodium salt of 2,5-diethoxycarbonyl-3,4-dihydroxythiophene as the starting material to react with haloalkane and then hydrolyze the product. Finally, quinoline and $Cu_2O$ were respectively used as solvent and catalyst for the decarboxylation reaction to obtain EDOT. However, the amount of the solvent residue was too high, the solvent was toxic, and the yield was only limitedly improved. Therefore, this method was not suitable for mass production (*J. Chem. Soc. Perkin Trans.* 1 2001, 2595).

Accordingly, a method of preparing 3,4-ethylenedioxythiophene (EDOT) with high yield and fast reaction rate is still needed.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present invention is directed to a method of preparing 3,4-ethylenedioxythiophene for increasing the yield.

Accordingly, the preparation method comprises the following steps.

(1) 2,2'-thiodiacetic acid and ethanol are mixed, and then sulfuric acid is added as a catalyst in a microwave reactor. The microwave reactor is heated by a 2.45 GHz microwave at a power of 500-1000 W to perform an esterification reaction for 15-30 minutes to obtain diethyl thioglycolate.

(2) The diethyl thioglycolate and diethyl oxalate are mixed, and then added to a first solution containing a first electron donor in the microwave reactor. The microwave reactor is heated by the 2.45 GHz microwave at a power of 100-500 W to perform a condensation reaction for 20-60 minutes to obtain 2,5-diethoxycarbonyl-3,4-dihydroxythiophene.

(3) The 2,5-diethoxycarbonyl-3,4-dihydroxythiophene and 1,2-dihaloethane are mixed, and then added to a second solution containing a second electron donor is added in the microwave reactor. The microwave reactor is heated by the 2.45 GHz microwave at a power of 500-1000 W to perform an etherification reaction for no more than 30 minutes to obtain 2,5-diethoxycarbonyl-3,4-ethylenedioxythiophene.

(4) The 2,5-diethoxycarbonyl-3,4-ethylenedioxythiophene and NaOH are mixed in the microwave reactor. The microwave reactor is heated by the 2.45 GHz microwave at a power of 500-1200 W to perform hydrolysis reaction for no more than 20 minutes to obtain 2,5-dicarboxy-3,4-ethylenedioxythiophene.

(5) The 2,5-dicarboxy-3,4-ethylenedioxythiophene and $Cu_2Cr_2O_5$ are mixed in the microwave reactor. The microwave reactor is heated by the 2.45 GHz microwave at a power of 500-1200 W to perform decarboxylation reaction for no more than 30 minutes to obtain 3,4-ethylenedioxythiophene.

In the foregoing, the preparation method at least has the advantages of mild reaction condition and environmental protecting process to decrease the environmental pollution. Furthermore, the preparation method has the advantages of fast reaction rate and high yield. Thus, 3,4-ethylenedioxythiophene can be efficiently prepared.

Accordingly, the preparation method above can sufficiently solve the prior art problems of preparing 3,4-ethylenedioxythiophene. The problems include toxic or unstable reactants, long reaction time, high cost, and low yield. Therefore, the 3,4-ethylenedioxythiophene cannot be mass-produced and thus supply efficiently.

It is to be understood that both the foregoing general description and the following detailed description are by examples, and are intended to provide further explanation of the invention as claimed. Many of the attendant features will be more readily appreciated as the same becomes better understood by reference to the following detailed description considered in connection with the accompanying drawings.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to the aspects above, the method of preparing 3,4-ethylenedioxythiophene (EDOT) in this disclosure comprises the following steps:

2,2'-thiodiacetic acid and ethanol are mixed, and then sulfuric acid is added as a catalyst in a microwave reactor. The microwave reactor is heated by a 2.45 GHz microwave at a power of 500-1000 W to perform an esterification reaction for 15-30 minutes to obtain diethyl thioglycolate. The is reaction is shown in the chemical formula (A).

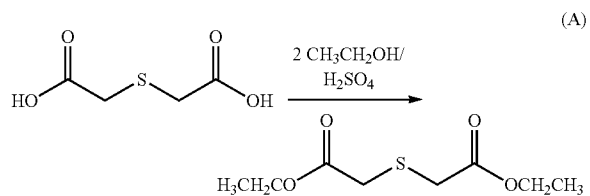

(A)

According to this disclosure, the power of the microwave reactor can be adjusted to undergo reactions inside the microwave reactor. Microwave heating has been massively used to replace conventionally heating method, such as water-bath heating, oil-bath heating, Bunsen burner heating, and heat-pack heating etc., in organic synthesis field. Microwave heating utilize vibrating polar molecules in a reaction solution by electromagnetic wave to generate heat, which is due to molecular collisions. Therefore, the reaction solution can be uniformly heated and reaches a desired high temperature in a short time to overcome the gradient temperature problem resulting from non-uniformly heating by conventional heating methods. Furthermore, microwave heating has the advantages of stable intermediates, and decreased heating and reacting time. Therefore, microwave heating, instead of conventional heating, used in this disclosure can also decrease operation dangers.

The esterification reaction in the chemical formula (A) is Fisher esterification. The acid catalyst in the esterification reaction is used to protonize the carbonyl group of the carboxylic acid to increase the electrophilicity of the carbon of the carbonyl group and thus the reaction rate. The acid catalyst can be used here comprises, but not limited to, $H_2SO_4$, HCl, 4-methylbenzenesulfonic, or any combinations thereof.

The conversion rate of the Fisher esterification can be decreased by the reverse reaction between the ester product and water. Therefore, a dehydrating device is needed in the esterification to decrease the reverse reaction. However, when the esterification is heated by microwave in this invention, no dehydrating device is needed to get a better yield.

The "yield" is defined as a ratio of the actual weight of the obtained product and the theoretical calculated weight of the product. The actual weight of the obtained product is the weight of the purified product, which does not contain any impurities such as other side products or solvent. The calculated formula of the yield is shown in formula (I):

Yield (%)=product's actual weight/product's theoretical weight×100%    (I)

In the esterification reaction, a better yield can be obtained when the equivalent ratio of the 2,2'-thiodiacetic acid and the ethanol is 1/12-1/6.

In the esterification, $H_2SO_4$ is used as the catalyst. However, if the added mount of $H_2SO_4$ is too much, the ester product will be hydrolyzed. to decrease the yield. Therefore, the equivalent ratio of the sulfuric acid and the 2,2'-thiodiacetic acid is preferably no more than 1:1, and more preferably to be 0.25-1, to get a better yield.

According to an embodiment, the solvent can be toluene, which can be azeotropically distillated to increase the dehydration rate and thus the yield.

The diethyl thioglycolate and diethyl oxalate are mixed, and then added to a first solution containing a first electron donor in the microwave reactor. The microwave reactor is heated by the 2.45 GHz microwave at a power of 100-500 W to perform a condensation reaction for 20-60 minutes to obtain 2,5-diethoxycarbonyl-3,4-dihydroxythiophene. The reaction is shown in the chemical formula (B).

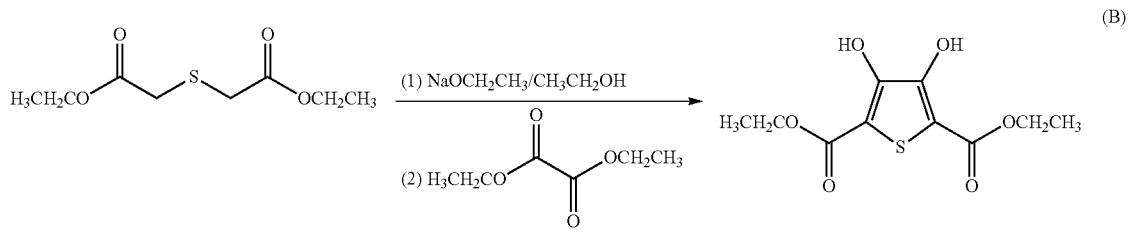

(B)

The condensation reaction is Hinsberg condensation. In this condensation, the equivalent ratio of the diethyl thioglycolate and diethyl oxalate is preferably to be 1/2-1 to get a better yield.

In this disclosure, an electron donor is a reductant to provide electron to another reactant molecule. At the same time, the electron donor is oxidized. Narrowly speaking, an electron donor is a Lewis base. The first electron donor in this disclosure provides electrons to diethyl thioglycolate, which make diethyl thioglycolate obtain reactive radicals and easily react with diethyl oxalate to obtain 2,5-diethoxycarbonyl-3,4-dihydroxythiophene.

In this disclosure, the equivalent ratio of the first electron donor and the diethyl thioglycolate is not less than 2, and preferably to be 2-4. The first electron donor comprises, but not limited to, metal alkoxide, alkali metal hydroxide, alkaline earth metal hydroxide, bicarbonate, carbonate, organic amine, or any combinations thereof.

The metal alkoxide used as the first electron donor comprises, but not limited to, sodium ethoxide.

The alkali metal hydroxide used as the first electron donor comprises, but not limited to, sodium hydroxide, or potassium hydroxide.

The alkaline earth metal hydroxide used as the first electron donor comprises, but not limited to, magnesium hydroxide.

The bicarbonate used as the first electron donor comprises, but not limited to, sodium bicarbonate, or potassium bicarbonate.

The carbonate used as the first electron donor comprises, but not limited to, sodium carbonate, or potassium carbonate.

The organic amine used as the first electron donor comprises, but not limited to, triethylamine.

A first solvent used in the first solution containing the first electron donor above is a solvent that can completely dissolve or stably disperse the first electron donor. There are no particular limitations for the first solvent used for the first solution. Therefore, the first solvent can be, but not limited to, water, methanol, ethanol, acetone, isopropyl alcohol, or toluene.

In this condensation reaction, the diethyl oxalate would be decomposed since the high operation temperature to decrease the yield. Therefore, the operation temperature of the condensation reaction is preferably not higher than 80° C. Furthermore, when the operation temperature of the Hinsberg condensation is 60-80° C., the ethoxy group of the diethyl oxalate can leave more easily to urge the condensation reaction forward. Therefore, the operation temperature of the condensation reaction is more preferably at 60-80° C.

Next, the 2,5-diethoxycarbonyl-3,4-dihydroxythiophene and 1,2-dihaloethane are mixed, and then added to a second solution containing a second electron donor is added in the microwave reactor. The microwave reactor is heated by the 2.45 GHz microwave at a power of 500-1000 W to perform an etherification reaction for no more than 30 minutes to obtain 2,5-diethoxycarbonyl-3,4-ethylenedioxythiophene. The reaction is shown in the chemical formula (C) below.

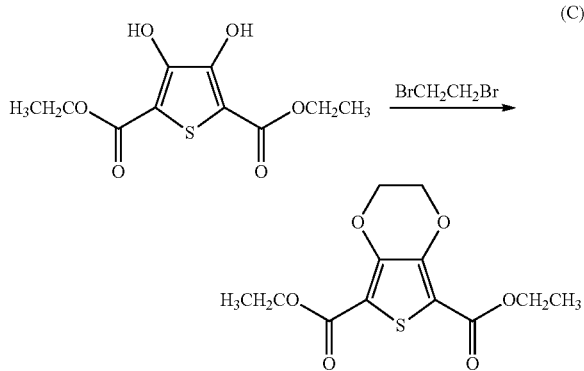

The etherification reaction is Williamson etherification. In this etherification reaction, the equivalent ratio of the 2,5-diethoxycarbonyl-3,4-dihydroxythiophene and 1,2-dihaloethane in the step (3) is 1/3-1 to gain a better yield.

In this disclosure, the 1,2-dihaloethane can be 1,2-dichloroethane, 1,2-dibromoethane, or 1,2-diiodoethane. In this reaction, the reaction's rate is according to the leaving ability of halides such as Cl⁻, Br⁻, and I⁻. The leaving ability of a leaving group is correlated with the $pK_a$ of its conjugate acid. The lower the $pK_a$ of its conjugate acid, the better the leaving group is. In this case, the acid strength is HI>HBr>HCl ($pK_a$: HI<HBr<HCl), so the leaving ability of the leaving group is I⁻>Br⁻>Cl⁻.

However, 1,2-diiodoalkanes are hard to synthesize, and thus have the highest prices among the three kinds of 1,2-dihaloethanes and are hard to be obtained. Moreover, 1,2-dichloroalkanes cannot easily undergo $S_N2$ reaction. Therefore, the 1,2-dibromoalkanes are the better reactant of the etherification reaction having the advantages of both convenience and reaction efficiency.

Moreover, the second electron donor provides electrons to the 2,5-diethoxycarbonyl-3,4-dihydroxythiophene to form a reactive radical. That helps 2,5-diethoxycarbonyl-3,4-dihydroxythiophene undergo nucleophilic reaction more easily to form 2,5-diethoxycarbonyl-3,4-ethylenedioxythiophene with 1,2-dihaloethane, which lost the electrons with the leaving of the leaving group.

In the etherification, the equivalent ratio of the second electron donor and 2,5-diethoxycarbonyl-3,4-dihydroxythiophene is preferably to be no less than 2, and more preferably to be 2-4.

The second electron donor comprises, but not limited to, metal alkoxide, alkali metal hydroxide, alkaline earth metal hydroxide, bicarbonate, carbonate, organic amine, or any combinations thereof.

The metal alkoxide used as the second electron donor comprises, but not limited to, sodium ethoxide.

The alkali metal hydroxide used as the second electron donor comprises, but not limited to, sodium hydroxide, or potassium hydroxide.

The alkaline earth metal hydroxide used as the second electron donor comprises, but not limited to, magnesium hydroxide.

The bicarbonate used as the second electron donor comprises, but not limited to, sodium bicarbonate, or potassium bicarbonate.

The carbonate used as the second electron donor comprises, but not limited to, sodium carbonate, or potassium carbonate.

The organic amine used as the second electron donor comprises, but not limited to, triethylamine.

Furthermore, the first and second electron donors can be chosen to be the same kind or different kinds of electron donor, depending on the need.

A second solvent used in the second solution containing the second electron donor above is a solvent that can completely dissolve or stably disperse the second electron donor. There are no particular limitations for the second solvent used for the second solution. Therefore, the second solvent can be, but not limited to, water, methanol, ethanol, acetone, isopropyl alcohol, or toluene. Furthermore, the first and second solvents can be chosen to be the same kind or different kinds of solvent, depending on the need.

The 2,5-diethoxycarbonyl-3,4-ethylenedioxythiophene and NaOH are mixed in the microwave reactor. The microwave reactor is heated by the 2.45 GHz microwave at a power of 500-1200 W to perform hydrolysis reaction for no more than 20 minutes to obtain 2,5-dicarboxy-3,4-ethylenedioxythiophene. The reaction is shown in the chemical formula (D).

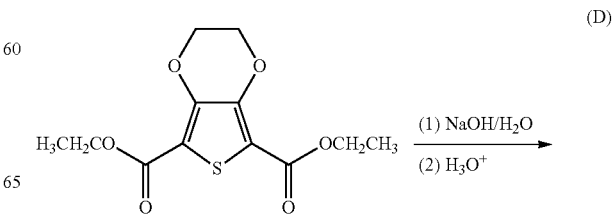

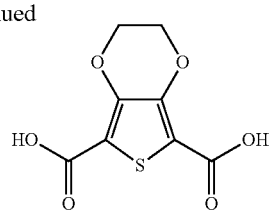

In this hydrolysis reaction, the equivalent ratio of the 2,5-diethoxycarbonyl-3,4-ethylenedioxythiophene and NaOH is preferred to be 1/5-1/3 to gain a better yield.

The reaction time of the hydrolysis reaction is better to be no more than 20 minutes, and more preferably to be 5-10 minutes to more efficiently produce the product.

Next, the 2,5-dicarboxy-3,4-ethylenedioxythiophene and $Cu_2Cr_2O_5$ are mixed in the microwave reactor. The microwave reactor is heated by the 2.45 to GHz microwave at a power of 500-1200 W to perform decarboxylation reaction for no more than 30 minutes to obtain 3,4-ethylenedioxythiophene.

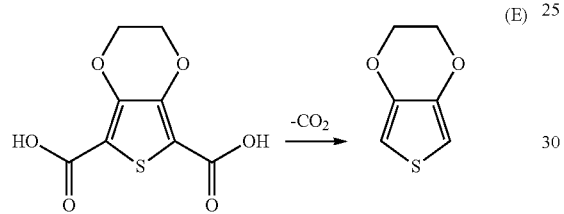

(E)

$Cu_2Cr_2O_5$ is conventionally used as the catalyst of decarboxylation reaction. In this decarboxylation reaction, the equivalent ratio of $Cu_2Cr_2O_5$ and the 2,5-dicarboxy-3,4-ethylenedioxythiophene is preferred to be 0.2-0.7 to gain a better yield.

The solvent can be used in this decarboxylation reaction comprises, but not limited to, dimethyl formamide (DMF), quinolone, or dimethyl sulfoxide (DMSO).

After reading the disclosure, persons skilled in the art can understand that a temperature control system or a pressuring system can be installed on the microwave reactor to avoid dangers due to fast heating rate or high temperature during the operation period of microwave reactor at a high power condition to perform the above mentioned esterification, condensation, etherification, hydrolysis, and decarboxylation reactions.

In order to overcome the problems of the prior arts, this invention has superiority over the prior arts.

Some embodiments are listed below to illustrate more details of this invention. It is to be understood that the following detailed description are by examples, and not used to limit this invention. The scope of this invention is defined in the appended claims of this invention.

EXAMPLES

A. Esterification: Preparation of Diethyl Thioglycolate

Example A1

15.015 g of 2,2'-thiodiacetic acid (Acros, Belgium), 55.284 g of ethanol (ECHO, Taiwan), and 4.9 g of sulfuric acid (Sigma-Aldrich, Switzerland) were added into 20 g of toluene (ECHO, Taiwan) and then stirred for mixing and dissolving the reagents above. The obtained solution was moved into a microwave reactor and heated by a 2.45 GHz microwave at a power of 500 W for 30 minutes.

A Dean-Stark receiver was installed outside the microwave reactor for dehydrating. The temperature of the heated solution was 86-87° C. and refluxed. The solution was cooled down after the reaction, and then its pH value was adjusted to 7.0-7.5 by adding $NaOH_{(aq)}$ in order to stop esterification. The solution was then extracted by ethyl acetate/n-hexane (9/1) and saturated salt water for three times. The obtained organic layer was dried by anhydrous magnesium sulfate, filtered, evaporated to remove solvent, and then vacuumed under a reduced pressure to obtain 17.1 g diethyl thioglycolate. The yield is 83.0%.

Example A2

The details were the same as Example A1, but the power of the microwave was 750 W and the reaction time was 20 minutes. The yield was 92.7%.

Example A3

The details were the same as Example A1, but the power of the microwave was 850 W and the reaction time was 17 minutes. The yield was 87.6%.

Example A4

The details were the same as Example A1, but the power of the microwave was 850 W and the reaction time was 20 minutes. The yield was 89.2%.

Example A5

The details were the same as Example A1, but the power of the microwave was 1000 W and the reaction time was 15 minutes. The yield was 81.6%.

Example A6

The details were the same as Example A2, but toluene and Dean-Stark receiver were not used. The yield was 95.1%.

Comparative Examples A1

The details were the same as Example A1, but the solution was heated by an oil bath, instead of microwave, to control the heating temperature was about 80° C. for 20 minutes. A Dean-Stark receiver was installed for dehydrating. The yield was 61.2%.

Comparative Examples A2

The details were the same as Comparative Example A1, but the heating time was 240 minutes. The yield was 75.0%.

Comparative Examples A3

The details were the same as Comparative Example A1, but toluene and Dean-Stark receiver were not used. The yield was 50.8%

The reaction conditions of the examples and the comparative examples are summarized in Table 1 below.

TABLE 1

Reaction conditions of the examples and the comparative examples in the esterification reaction

| | Microwave power (W) | Reaction time (min) | Reaction Temperature (° C.) | Dean-Stark Receiver | toluene (g) | Yield (%) |
|---|---|---|---|---|---|---|
| Example A1 | 500 | 30 | 86 | ○ | 20 | 83.0 |
| Example A2 | 750 | 20 | 86 | ○ | 20 | 92.7 |
| Example A3 | 850 | 17 | 86 | ○ | 20 | 87.6 |
| Example A4 | 850 | 20 | 86 | ○ | 20 | 89.2 |
| Example A5 | 1000 | 15 | 86 | ○ | 20 | 81.6 |
| Example A6 | 750 | 20 | 86 | X | 0 | 95.1 |
| Comparative Example A1 | — | 20 | 80 | ○ | 20 | 61.2 |
| Comparative Example A2 | — | 240 | 80 | ○ | 20 | 75.0 |
| Comparative Example A3 | — | 20 | 80 | X | 0 | 50.8 |

From Table 1, it can be known that the esterification heated by conventional oil bath (Comparative Examples A1, A2, and A3) does not have industrial utility, since the reaction time was too long and the yield was limited. However, the esterification heated by microwave can gain a better yield and even does not need the Dean-Stark receiver. Therefore, using microwave can solve the problem of installing dehydrating apparatus and decrease the used amount of the solvent to facilitate operation, energy saving, and environmental protection. For example, Example 6 does not need Dean-Stark receiver and gain a high yield of 91.5%.

B. Condensation: Preparation of 2,5-diethoxycarbonyl-3,4-dihydroxythiophene

Example B1

10.3 g of Example A6's product and 10.96 g of diethyl oxylate (Acros, Belgime) were mixed and then put in water bath at a temperature of 0-10° C. Sodium ethoxide (Acros, Belgime) in ethanol solution was dropwise added to the mixture and sufficiently stirred the solution. The solution was then moved into a microwave reactor and heated by a 2.45 GHz microwave of a power of 100 W for 60 minutes. The reaction temperature was maintained at 68° C. Next, the solution was added with HCl (Scharlau, Australia) to adjust pH value to 7.0-7.5 in order to stop the reaction, and then evaporated to remove ethanol. The dried mixture was added with HCl to adjust pH value to 2.5-3.0 and then added with 400 mL of deionized water to precipitate product. After filtering, the obtained product was dried in an oven to obtain 8.58 g product of 2,5-diethoxycarbonyl-3,4-dihydroxythiophene. The yield was 65.3%.

Examples B2-B5

The practicing details were the same as Example B1, but the power of the microwave was set to 200 W, 300 W, 400 W, and 500 W, respectively. The yields are listed in Table 2 below.

Examples B6-B10

The practicing details were respectively the same as Examples B1 to B5, but the reaction time was adjusted to 40 minutes. The yields are listed in Table 2 below.

Examples B11-B12

The practicing details were respectively the same as Examples B2 and B4, but the reaction time was set to 20 minutes. The yields are listed in Table 2 below.

Comparative Example B1

The practicing details were the same as Example B1, but the microwave was replaced by an oil bath, such that the condensation reaction was performed at a temperature of 80° C. for 60 minutes. The yield was 63.8%.

Comparative Example B2

The practicing details were the same as Comparative Example B1, but the heating time of the oil bath was 20 minutes. The yield was 60.6%.

Comparative Examples B3-B5

The practicing details were the same as Example B1, but the power of the microwave was set to 700 W, and the reaction times were 60, 40, and 20 minutes, respectively. The yields are listed in Table 2 below.

The reaction conditions of the examples and the comparative examples in the condensation reaction are summarized in Table 2.

TABLE 2

Reaction conditions of the examples and the comparative examples in the condensation reaction

| | Microwave power (W) | Reaction time (min) | Yield (%) |
|---|---|---|---|
| Example B1 | 100 | 60 | 65.3 |
| Example B2 | 200 | 60 | 68.8 |
| Example B3 | 300 | 60 | 69.1 |
| Example B4 | 400 | 60 | 76.9 |
| Example B5 | 500 | 60 | 69.8 |
| Example B6 | 100 | 40 | 65.2 |
| Example B7 | 200 | 40 | 67.0 |
| Example B8 | 300 | 40 | 68.2 |
| Example B9 | 400 | 40 | 72.3 |
| Example B10 | 500 | 40 | 67.0 |
| Example B11 | 200 | 20 | 68.3 |
| Example B12 | 400 | 20 | 70.0 |
| Comparative Example B1 | — | 60 | 63.8 |
| Comparative Example B2 | — | 20 | 60.6 |

TABLE 2-continued

Reaction conditions of the examples and the comparative examples in the condensation reaction

| | Microwave power (W) | Reaction time (min) | Yield (%) |
|---|---|---|---|
| Comparative Example B3 | 700 | 60 | 63.2 |
| Comparative Example B4 | 700 | 40 | 63.2 |
| Comparative Example B5 | 700 | 20 | 63.1 |

From Table 2, it can be known that microwave with suitable adjusted power can be used to replace conventional heating way to perform the condensation reaction having a shorter reaction time and comparable yields or even better yields. That was, microwave heating can more efficiently gain needed yield. For example, Example B4 was a better example. The yield of Example B4 was 76.9%

C. Etherification: Preparation of 2,5-diethoxycarbonyl-3,4-ethylenedioxythiophene

Example C1

5.2 g of example B1's product, 4.5 g of 1,2-dibromoethane (TEDIA, USA), and 5.53 g of $K_2CO_3$ (SHOWA, Japan) were added with 9.44 g of DMF (Fisher Scientific, USA). After sufficiently stirring, the mixture was moved into a microwave reactor and heated by a 2.45 GHz microwave at a power of 500 W for 20 minutes, and the reaction temperature was maintained at 160° C. Next, the DMF was removed and water was then added to precipitate product. 4.36 g of 2,5-diethoxycarbonyl-3,4-ethylenedioxythiophene was obtained after filtering and drying, the yield was 76.2%.

Examples C2 and C3

The details were the same as Example C1, but the power of the microwave was 750 and 1000 W, respectively. The yields are listed in Table 3.

Comparative Examples C1 and C2

The details were the same as Example C1, but the power of the microwave was 1200 and 250 W, respectively. The yields are listed in Table 3.

Comparative Examples C3

The details were the same as Example C1, solution was heated by an oil bath, instead of microwave, to control the heating temperature at about 160° C. for 20 minutes. The yield was 70.3%

The etherification reaction conditions of the examples and the comparative examples are summarized in Table 3 below.

TABLE 3

Etherification reaction conditions of the examples and the comparative examples

| | Microwave power (W) | Reaction time (min) | Yield (%) |
|---|---|---|---|
| Example C1 | 500 | 20 | 76.2 |
| Example C2 | 750 | 20 | 79.3 |
| Example C3 | 1000 | 20 | 83.8 |
| Comparative Example C1 | 1200 | 20 | 70 |
| Comparative Example C2 | 250 | 20 | 53.2 |
| Comparative Example C3 | — | 20 | 70.3 |

From Table 3, it can be known that microwave with suitable adjusted power can be used to replace conventional heating way to perform the etherification reaction having better yields. Example C3 was a better example, and it can gain a yield of 83.8%. The reaction temperature could not be effectively reached when the microwave power of the Comparative Example C2 was set to 250 W, the yield was poorer. However, if the microwave power was too high, the high temperature would cause violent reaction to proceed side reaction and obtain side products, and the yield was thus decreased. Therefore, the preferred microwave power was 500-1000 W to obtain a better yield than conventional heating way.

D. Hydrolysis Reaction: Preparation of 2,5-dicarboxy-3,4-ethylenedioxythiophene

Example D1

4.0142 g of Example C is product, 1.684 g of NaOH(S-HOWA, Japan) were added into 70.18 g of deionized water in a round-bottomed reaction flask. After sufficiently stirring, the reaction solution was moved into a microwave reactor and heated by a 2.45 GHz microwave of a power of 500 W for 10 minutes. The reaction temperature was maintained at 100° C. Next, after cooling to room temperature, the reaction was stopped by using $HCl_{(aq)}$ to control pH at 2.0. 2.94 g of 2,5-dicarboxy-3,4-ethylenedioxythiophene was obtained after filtering and drying, and the yield was 91.3%.

Examples D2-D4

The details were the same as Example D1, but the microwave power was set to 500, 1000, and 1200 W, respectively, and the reaction time was adjusted to 5 minutes. The yields are listed in Table 4.

Comparative Example D1

The details were the same as Example D1, but the microwave power was set to 250 W. The yield was 80.3%.

Comparative Example D2

The details were the same as Example D1, but an oil bath was used to replace the microwave reactor. The heating temperature was 100° C., and the heating time was 5 minutes. The yield was 80.6%.

Comparative Example D3

The details were the same as Example D1, but an oil bath was used to replace the microwave reactor. The heating temperature was 100° C., and the heating time was 120 minutes. The yield was 89.3%.

The hydrolysis reaction conditions of the examples and the comparative examples are summarized in Table 4 below.

TABLE 4

Hydrolysis reaction conditions of the examples and the comparative examples

| | Microwave power (W) | Reaction time (min) | Yield (%) |
|---|---|---|---|
| Example D1 | 500 | 10 | 91.3 |
| Example D2 | 500 | 5 | 89.3 |
| Example D3 | 1000 | 5 | 91.8 |
| Example D4 | 1200 | 5 | 92.0 |
| Comparative Example D1 | 250 | 5 | 80.3 |
| Comparative Example D2 | — | 5 | 80.6 |
| Comparative Example D3 | — | 120 | 89.3 |

From Table 4, it can be known that the yield of the hydrolysis reaction heated by conventional Bunsen burner, oil bath and water bath could be 89.3%, but the heating time was 120 minutes to obtain this better yield. However, the microwave heating can greatly reduce the needed reaction time to obtain an even better yield. For example, Example D4 is a preferred embodiment, and its yield was 92%.

E. Decarboxylation: Preparation of 3,4-ethylenedioxythiophene

Example E1

4.6 g of Example D1's product and 0.62 g of $Cu_2Cr_2O_5$ (Acros, Belgime) were added into 18.44 g of dimethylformamide (DMF) in a round-bottom reaction flask. After sufficiently stirring, the solution was moved into a microwave rector and heated by a 2.45 GHz microwave of a power of 500 W for 20 minutes. The reaction temperature was maintained at 153° C. The obtained product was purified by column chromatography to obtain 2.31 g of 3,4-ethylenedioxythiophene. The yield was 85.3%.

Examples E2-E4

The details were the same as Example E1, but the microwave power was set to 750, 1000, and 1200 W, respectively. The yields are listed in Table 5.

Comparative Example E1

The details were the same as Example E1, but the microwave power was set to 250 W. The yield was 75.0%.

Comparative Example E2

The details were the same as Example E1, but an oil bath was used to replace the microwave reactor. The heating temperature was at 153° C. and the heating time was 20 minutes. The yield was 80.9%.

Comparative Example E3

The details were the same as Example E1, but an oil bath was used to replace the microwave reactor. The heating temperature was at 153° C. and the heating time was 150 minutes. The yield was 81.0%.

The decarboxylation reaction conditions of the examples and the comparative examples are summarized in Table 5 below.

TABLE 5

Decarboxylation reaction conditions of the examples and the comparative examples

| | Microwave power (W) | Reaction time (min) | Yield (%) |
|---|---|---|---|
| Example E1 | 500 | 20 | 85.3 |
| Example E2 | 750 | 20 | 90.6 |
| Example E3 | 1000 | 20 | 95.0 |
| Example E4 | 1200 | 20 | 83.0 |
| Comparative Example E1 | 250 | 20 | 75.0 |
| Comparative Example E2 | — | 20 | 80.9 |
| Comparative Example E3 | — | 150 | 81.0 |

From Table 5, it can be known that the reaction time of the decarboxylation reaction heated by conventional oil bath or Bunsen burner was too long, and the yield can only be limitedly increased. Therefore, the energy consumption was very large, and thus does not meet the requirements of the industrial utility and the environmental protection. However, the microwave reactor with suitably adjusted microwave power can be used to replace the conventional heating ways to perform the decarboxylation reaction to obtain better yields. Example E3 was a preferred embodiment, and its yield was 95.0%.

Furthermore, the reaction conditions and yields of the five reactions A to E heated by microwave and conventional ways were summarized in Tables 6 and 7 to make a comparison.

TABLE 6

Under the same reaction time and reaction temperature, comparing the yields of microwave heating and conventional heating.

| | | Yield (%) | |
|---|---|---|---|
| | Reaction time (min) | Microwave heating | Conventional heating |
| A. Etherification | 20 | 95.1 (Example A6) | 61.2 (Comparative Example A1) |
| B. Condensation | 60 | 76.9 (Example B4) | 63.8 (Comparative Example B1) |
| C. Etherification | 20 | 83.8 (Example C3) | 70.3 (Comparative Example C3) |
| D. Hydrolysis | 5 | 92.0 (Example D4) | 80.6 (Comparative Example D2) |
| E. Decarboxylation | 20 | 95.0 (Example E3) | 80.9 (Comparative Example E2) |
| Total Reaction | 125 | 53.56 | 17.89 |

From Table 6, it can be known that the yield of 3,4-ethylenedioxythiophene prepared by conventional heating ways was only 17.89%. However, under the same reaction time, the yield of 3,4-ethylenedioxythiophene prepared by microwave, instead of conventional heating ways, can be 53.56%, which was three times on the yield heated by conventional heating ways. Therefore, using microwave to replace conventional heating can greatly increase the production yield.

TABLE 7

Comparing the yields of the best embodiments performed by microwave heating and conventional heating.

|  | Reaction time (min) | | Yield (%) | |
| --- | --- | --- | --- | --- |
|  | Microwave heating | Conventional heating | Microwave heating | Conventional heating |
| A. Etherification | 20 | 240 | 95.1 (Example A6) | 75.0 (Comparative Example A1) |
| B. Condensation | 60 | 60 | 76.9 (Example B4) | 63.8 (Comparative Example B1) |
| C. Etherification | 20 | 20 | 83.8 (Example C3) | 70.3 (Comparative Example C3) |
| D. Hydrolysis | 5 | 120 | 92.0 (Example D4) | 89.3 (Comparative Example D2) |
| E. Decarboxylation | 20 | 150 | 95.0 (Example E3) | 81.0 (Comparative Example E2) |
| Total Reaction | 125 | 590 | 53.56 | 24.33 |

From Table 7, it can be known that the best yield of 3,4-ethylenedioxythiophene prepared by the conventional heating was only 24.33%, and the reaction time was 590 minutes. Therefore, the yield of the conventional heating cannot reach a satisfying yield even by prolonging the reaction time. Using microwave to perform synthesis of 3,4-ethylenedioxythiophene can increase the reaction rate, shorten the reaction time, and increase the total yield. The reaction time of the synthesis heated by microwave is only ⅕ of the reaction time of the synthesis heated by conventional heating ways. The yield of 3,4-ethylenedioxythiophene prepared by microwave heating was up to 53.56%. Therefore, the microwave heating makes the synthesis of 3,4-ethylenedioxythiophene have industrial utility and efficiently prepare 3,4-ethylenedioxythiophene.

The description above is only the preferred embodiments of this invention and not used to limit the scope of this invention. Some equivalent changes and modifications without departing from this invention can be made by any persons skilled in the art are within the scope of this invention.

What is claimed is:

1. A method of preparing 3,4-ethylenedioxythiophene, comprising:
   (1) mixing 2,2'-thiodiacetic acid and ethanol and then adding sulfuric acid as a catalyst in a microwave reactor heated by a 2.45 GHz microwave at a power of 500-1000 W to perform an esterification reaction for 15-30 minutes to obtain diethyl thioglycolate, wherein an equivalent ratio of the sulfuric acid and the 2,2'-thiodiacetic acid is no more than 1;
   (2) mixing the diethyl thioglycolate and diethyl oxalate and then adding to a first solution containing a first electron donor in the microwave reactor heated by the 2.45 GHz microwave at a power of 100-500 W to perform a condensation reaction for 20-60 minutes to obtain 2,5-diethoxycarbonyl-3,4-dihydroxythiophene;
   (3) mixing the 2,5-diethoxycarbonyl-3,4-dihydroxythiophene and 1,2-dihaloethane and then adding to a second solution containing a second electron donor in the microwave reactor heated by the 2.45 GHz microwave at a power of 500-1000 W to perform an etherification reaction for no more than 30 minutes to obtain 2,5-diethoxycarbonyl-3,4-ethylenedioxythiophene;
   (4) mixing the 2,5-diethoxycarbonyl-3,4-ethylenedioxythiophene and NaOH in the microwave reactor heated by the 2.45 GHz microwave at a power of 500-1200 W to perform a hydrolysis reaction for no more than 20 minutes to obtain 2,5-dicarboxy-3,4-ethylenedioxythiophene; and
   (5) mixing the 2,5-dicarboxy-3,4-ethylenedioxythiophene and $Cu_2Cr_2O_5$ in the microwave reactor heated by the 2.45 GHz microwave at a power of 500-1200 W to perform a decarboxylation reaction for no more than 30 minutes to obtain 3,4-ethylenedioxythiophene.

2. The method of claim 1, wherein an equivalent ratio of the 2,2'-thiodiacetic acid and the ethanol in the step (1) is 1/12-1/6.

3. A method of preparing 3,4-ethylenedioxythiophene, comprising:
   (1) mixing 2,2'-thiodiacetic acid and ethanol and then adding sulfuric acid as a catalyst in a microwave reactor heated by a 2.45 GHz microwave at a power of 500-1000 W to perform an esterification reaction for 15-30 minutes to obtain diethyl thioglycolate;
   (2) mixing the diethyl thioglycolate and diethyl oxalate and then adding to a first solution containing a first electron donor in the microwave reactor heated by the 2.45 GHz microwave at a power of 100-500 W to perform a condensation reaction for 20-60 minutes to obtain 2,5-diethoxycarbonyl-3,4-dihydroxythiophene, wherein an equivalent ratio of the diethyl thioglycolate and diethyl oxalate is 1/2-1;
   (3) mixing the 2,5-diethoxycarbonyl-3,4-dihydroxythiophene and 1,2-dihaloethane and then adding to a second solution containing a second electron donor in the microwave reactor heated by the 2.45 GHz microwave at a power of 500-1000 W to perform an etherification reaction for no more than 30 minutes to obtain 2,5-diethoxycarbonyl-3,4-ethylenedioxythiophene;
   (4) mixing the 2,5-diethoxycarbonyl-3,4-ethylenedioxythiophene and NaOH in the microwave reactor heated by the 2.45 GHz microwave at a power of 500-1200 W to perform a hydrolysis reaction for no more than 20 minutes to obtain 2,5-dicarboxy-3,4-ethylenedioxythiophene; and (5) mixing the 2,5-dicarboxy-3,4-ethylenedioxythiophene and $Cu_2Cr_2O_5$ in the microwave reactor heated by the 2.45 GHz microwave at a power of 500-1200 W to perform a decarboxylation reaction for no more than 30 minutes to obtain 3,4-ethylenedioxythiophene.

4. The method of claim 3, wherein an equivalent ratio of the first electron donor and the diethyl thioglycolate in the step (2) is not less than 2.

5. The method of claim 3, wherein an equivalent ratio of the first electron donor and the diethyl thioglycolate in the step (2) is 2-4.

6. A method of preparing 3,4-ethylenedioxythiophene, comprising:
  (1) mixing 2,2'-thiodiacetic acid and ethanol and then adding sulfuric acid as a catalyst in a microwave reactor heated by a 2.45 GHz microwave at a power of 500-1000 W to perform an esterification reaction for 15-30 minutes to obtain diethyl thioglycolate;
  (2) mixing the diethyl thioglycolate and diethyl oxalate and then adding to a first solution containing a first electron donor in the microwave reactor heated by the 2.45 GHz microwave at a power of 100-500 W to perform a condensation reaction for 20-60 minutes to obtain 2,5-diethoxycarbonyl-3,4-dihydroxythiophene;
  (3) mixing the 2,5-diethoxycarbonyl-3,4-dihydroxythiophene and 1,2-dihaloethane and then adding to a second solution containing a second electron donor in the microwave reactor heated by the 2.45 GHz microwave at a power of 500-1000 W to perform an etherification reaction for no more than 30 minutes to obtain 2,5-diethoxycarbonyl-3,4-ethylenedioxythiophene, wherein an equivalent ratio of the 2,5-diethoxycarbonyl-3,4-dihydroxythiophene and 1,2-dihaloethane is 1/3 -1;
  (4) mixing the 2,5-diethoxycarbonyl-3,4-ethylenedioxythiophene and NaOH in the microwave reactor heated by the 2.45 GHz microwave at a power of 500-1200 W to perform a hydrolysis reaction for no more than 20 minutes to obtain 2,5-dicarboxy-3,4-ethylenedioxythiophene; and
  (5) mixing the 2,5-dicarboxy-3,4-ethylenedioxythiophene and $Cu_2Cr_2O_5$ in the microwave reactor heated by the 2.45 GHz microwave at a power of 500-1200 W to perform a decarboxylation reaction for no more than 30 minutes to obtain 3,4-ethylenedioxythiophene.

7. The method of claim 6, wherein an equivalent ratio of the second electron donor and 2,5-diethoxycarbonyl-3,4-dihydroxythiophene in the step (3) is not less than 2.

8. The method of claim 6, wherein an equivalent ratio of the second electron donor and 2,5-diethoxycarbonyl-3,4-dihydroxythiophene in the step (3) is 2-4.

9. A method of preparing 3,4-ethylenedioxythiophene, comprising:
  (1) mixing 2,2'-thiodiacetic acid and ethanol and then adding sulfuric acid as a catalyst in a microwave reactor heated by a 2.45 GHz microwave at a power of 500-1000 W to perform an esterification reaction for 15-30 minutes to obtain diethyl thioglycolate;
  (2) mixing the diethyl thioglycolate and diethyl oxalate and then adding to a first solution containing a first electron donor in the microwave reactor heated by the 2.45 GHz microwave at a power of 100-500 W to perform a condensation reaction for 20-60 minutes to obtain 2,5-diethoxycarbonyl-3,4-dihydroxythiophene;
  (3) mixing the 2,5-diethoxycarbonyl-3,4-dihydroxythiophene and 1,2-dihaloethane and then adding to a second solution containing a second electron donor in the microwave reactor heated by the 2.45 GHz microwave at a power of 500-1000 W to perform an etherification reaction for no more than 30 minutes to obtain 2,5-diethoxycarbonyl-3,4-ethylenedioxythiophene;
  (4) mixing the 2,5-diethoxycarbonyl-3,4-ethylenedioxythiophene and NaOH in the microwave reactor heated by the 2.45 GHz microwave at a power of 500-1200 W to perform a hydrolysis reaction for no more than 20 minutes to obtain 2,5-dicarboxy-3,4-ethylenedioxythiophene, wherein an equivalent ratio of the 2,5-diethoxycarbonyl-3,4-ethylenedioxythiophene and NaOH is 1/5-1/3; and
  (5) mixing the 2,5-dicarboxy-3,4-ethylenedioxythiophene and $Cu_2Cr_2O_5$ in the microwave reactor heated by the 2.45 GHz microwave at a power of 500-1200 W to perform a decarboxylation reaction for no more than 30 minutes to obtain 3,4-ethylenedioxythiophene.

10. A method of preparing 3,4-ethylenedioxythiophene, comprising:
  (1) mixing 2,2'-thiodiacetic acid and ethanol and then adding sulfuric acid as a catalyst in a microwave reactor heated by a 2.45 GHz microwave at a power of 500-1000 W to perform an esterification reaction for 15-30 minutes to obtain diethyl thioglycolate;
  (2) mixing the diethyl thioglycolate and diethyl oxalate and then adding to a first solution containing a first electron donor in the microwave reactor heated by the 2.45 GHz microwave at a power of 100-500 W to perform a condensation reaction for 20-60 minutes to obtain 2,5-diethoxycarbonyl-3,4-dihydroxythiophene;
  (3) mixing the 2,5-diethoxycarbonyl-3,4-dihydroxythiophene and 1,2-dihaloethane and then adding to a second solution containing a second electron donor in the microwave reactor heated by the 2.45 GHz microwave at a power of 500-1000 W to perform an etherification reaction for no more than 30 minutes to obtain 2,5-diethoxycarbonyl-3,4-ethylenedioxythiophene;
  (4) mixing the 2,5-diethoxycarbonyl-3,4-ethylenedioxythiophene and NaOH in the microwave reactor heated by the 2.45 GHz microwave at a power of 500-1200 W to perform a hydrolysis reaction for no more than 20 minutes to obtain 2,5-dicarboxy-3,4-ethylenedioxythiophene; and
  (5) mixing the 2,5-dicarboxy-3,4-ethylenedioxythiophene and $Cu_2Cr_2O_5$ in the microwave reactor heated by the 2.45 GHz microwave at a power of 500-1200 W to perform a decarboxylation reaction for no more than 30 minutes to obtain 3,4-ethylenedioxythiophene, wherein an equivalent ratio of $Cu_2Cr_2O_5$ and the 2,5-dicarboxy-3,4-ethylenedioxythiophene is 0.2-0.7.

* * * * *